United States Patent [19]

Globus et al.

[11] Patent Number: 5,023,355

[45] Date of Patent: Jun. 11, 1991

[54] STABILIZED B-CAROTENE

[76] Inventors: Alfred R. Globus, 26-53 210th St., Bayside, N.Y. 11360; Joseph Vernice, 80 Parkview Dr. W., Shirley, N.Y. 11967

[21] Appl. No.: 541,039

[22] Filed: Jun. 20, 1990

[51] Int. Cl.$^5$ ............................................. C07D 307/02
[52] U.S. Cl. ........................................ 549/478; 549/476
[58] Field of Search ................................. 549/476, 478

[56] References Cited

U.S. PATENT DOCUMENTS

| | | | |
|---|---|---|---|
| 2,873,297 | 2/1959 | Ramsden | 549/497 |
| 2,894,012 | 7/1959 | Ramsden et al. | 549/497 |
| 2,959,598 | 11/1960 | Ramsden | 549/497 |
| 3,649,647 | 3/1972 | Masahori et al. | 549/476 |
| 4,879,289 | 11/1989 | Lang et al. | 549/398 |
| 4,939,277 | 7/1990 | Imaki et al. | 549/476 |
| 4,958,033 | 9/1990 | Takisawa et al. | 549/497 |

*Primary Examiner*—C. Warren Ivy
*Assistant Examiner*—Raymond Covington
*Attorney, Agent, or Firm*—Evelyn M. Sommer

[57] ABSTRACT

A process for the preparation of stabilized B-carotene wherein polysorbate is heated under an inert atmosphere to about 100° to about 120° C. in the presence of butylated hydroxytoluene for a period of time sufficient to allow substantially all of the water present in the polysorbate to be driven off. The temperature is then increased to about 160° to about 180° C. and the resultant polysorbate product further heated at this temperature while maintaining the inert atmosphere and under strong stirring for 1 to 1½ hours. The thus heated polysorbate is then cooled rapidly to about 100° to about 120° C. and 2.0 to 4.0% by weight of B-carotene, based on the weight of the polysorbate, introduced under strong stirring in the presence of para-aminobenzoic acid and a conventional antioxidant such as butylhydroxyquinone under contained maintenance of the inert atmosphere. The resulting liquid composition is cooled to room temperature. A dark yellow, stable B-carotene liquid is recovered.

The stabilized B-carotene product of the invention is useful as a precursor of vitamin A, can be employed as a colorant, for example a food colorant, and as a medicament for use both in human and animal medicine.

6 Claims, No Drawings

STABILIZED B-CAROTENE

The present invention relates to stable B-carotene and a process for its production.

BACKGROUND OF THE INVENTION

Retinol (Vitamin A) is known to be necessary to the biochemistry of human vision. Through a series of reactions the retinol is converted through retinal isomers to rhodopsin ("visual purple"). Irradiation of the rhodopsin with visible light in turn causes a series of isomerization reactions through the retinal isomers to opsin resulting in excitation of the retinal rod cells and generation of a visual nerve impulse. A deficiency of Vitamin A in the system leads to reduced visual sensitivity (especially night blindness) and in extreme cases (e.g., keratomalacia or xerophthalmia) to complete blindness.

Vitamin A is also known to be necessary to the proper function of the epithelial tissues. Deficiency of Vitamin A in such cases results in disorders such as reduced resistance to infection through epithelial surfaces.

Increases in the level of Vitamin A in the body may to some extent be obtained by administering doses of Vitamin A directly to an individual. However, there is a limited bodily tolerance to Vitamin A, and overdoes of Vitamin A can lead to toxic effects. Since the tolerance level varies widely among individuals, it is not generally advisable to administer substantial doses of Vitamin A except under carefully controlled circumstances.

It is well known that carotene is the precursor of Vitamin A. (There are several carotene isomers, including the alpha-, beta- and gamma-carotene isomers. Of these the beta-carotene isomer has the most Vitamin A activity and is also the most common. As used herein, the term "carotene" is limited to B-Carotene. Carotene is oxidized by liver enzymes to produce Vitamin A. Significantly, however, the enzyme metabolism produces only the amount of Vitamin A that can be utilized by the body; it does not produce an overdose of Vitamin A. Consequently, an individual can be administered doses of carotene in quantities large enough to produce optimum levels of Vitamin A in the body without the risk of a toxic Vitamin A reaction. Excess carotene which is administered is stored in fatty tissues and organs.

The carotenes, particularly beta-carotene, are present in many common foods, primarily the green and yellow vegetables such as tomatoes, citrus fruits, carrots, squash, turnips, broccoli and spinach. The concentration of carotene in these vegetables is relatively low, and a person must consume substantial quantities of the vegetables to have a high intake level of carotene. The normal diet for most people does not include such large quantities of these vegetables, so there has developed a commercial market for concentrated carotene dietary supplements, particularly those in which the carotene is beta-carotene because of its high Vitamin A activity. These supplements normally have been produced by extraction of carotene from vegetables such as carrots by use of petrochemical solvents. The resulting carotene, usually in crystalline form, can be expected to be associated with at least residual quantities of such solvents. This is particularly true when the carotene is administered in a dosage form in which it is dispersed in a petrochemical or other "synthetic" oil. The presence, even in minute amounts, of such petrochemical residues in the carotene supplements has caused apprehension among users of the supplements.

It is also known that certain algae, especially those in the classes Rhodophyta (red algae) and Chlorophyta (green algae), are good sources of carotene. The carotene content of species of the genus Dunaliella have been reported in U.S. Pat. Nos. 4,115,949 and 4,119,895 and in *Acta Chem. Scand.* 23, 7, 2544-2545 (1979). Similar data for the genus Chlorococcum has been disclosed in U.S. Pat. No. 2,949,700. In the past, however, all extraction processes to produce the carotene from algae have involved the use of petrochemical solvents, which results in the same contamination problems discussed above for the vegetable extractions. In addition, many of the algal extraction processes have involved drying of the alga, which has been found to degrade the carotene.

In addition to the use of carotene as a precursor for Vitamin A, there have recently been reports in the literature that suggest that carotene is itself useful in the prevention of certain types of cancers which are believed to be promoted by oxidizing free radicals. It is postulated that carotene, which has an affinity for such free radicals, may serve to reduce the free radical level in the body, thereby reducing the occurrence of free radical initiation of malignancies. There are studies currently underway which are expected to provide more information regarding the effects of carotene on such cancers.

It would therefore be of benefit to have carotene available in a form which would be safe and therapeutically useful for humans, and which would not have the disadvantages noted.

More particularly, it would be of benefit to have such carotene available in a stable form. B-carotene is extremely sensitive to oxidation. It is usually stored in tightly sealed containers. However, even with such precautionary measures, there is sufficient oxygen available to cause a substantial decrease in activity in about eight (8) days.

It is an object of the present invention to prepare relatively highly pure, clear and stable B-carotene.

We have found that this object is achieved by a process for the preparation of B-carotene which comprises reacting 2-10 parts of B-carotene, preferably in the presence of an antioxidant such as butylated hydroxytoluene with 98-90 parts of polysorbate.

As used herein, B-carotene has the chemical formula

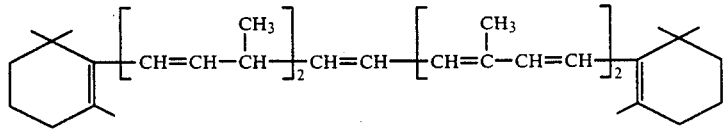

and polysorbate the chemical formula

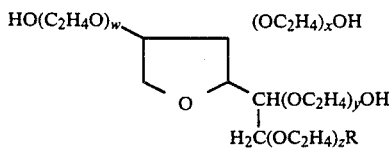

[Sum of w, x, y, z is 20; R is (C₁₇H₃₃)COO]

The reaction between the B-carotene and the polysorbate is carried out in the following manner:

(1) The polysorbate (90–99 parts) is heated with an antioxidant, such as buylated hydroxytoluene (BHT), in order to remove any water. This is carried out under stirring at normal atmospheric to moderately increased pressures and at temperatures in the 100° C. to 120° C. range, or under vacuum at reduced temperatures. Removal of the water separated out is facilitated by bubbling dry argon or nitrogen through the polysorbate.

(2) Once the water is substantially completely removed, the B-carotene (1–10 parts) is added. Conditions are maintained until the B-carotene is dispersed in the solution. At this time the temperature is increased to about 160°–180° C. at atmospheric pressure. Once again, the inert atmosphere is maintained. Conditions are held constant for approximately 1–2 hours before the heat is removed;

(3) Immediately thereafter, there are added 2–5 parts t-butylhydroquinone (TBHQ) and 2–5 parts p-aminobenzoic acid (PABA), under an inert atmosphere. The stirring is continued as the solution is allowed to cool below 30° C.

(4) The resulting deep orange syrupy solution is assayed for activity and subsequently packaged in dark containers.

Examples of particularly suitable polysorbates are: glyceryl polyoxyethylene glycol ricinoleate, glycerol polyoxyethylene glycol hydroxystearate, polyoxyethylene-20 sorbitan mono-oleate, polyoxyethylene-20 sorbitan monostearate, polyoxyethylene-sorbitan monolaurate, and the adduct monohydroxystearic acid with 15 units of ethylene oxide.

Examples of conventional antioxidants which can be used in the process according to the invention are butylhydroxytoluene, butylhydroxyanisole and d,1-α-tocopherol. The antioxidants are generally used in amounts of from 10 to 20% by weight, based on the B-carotene employed.

Despite the belief held by the skilled in the at, no isomerization of the B-carotene takes place at these temperatures. The stabilized B-carotene produced in accordance with the invention has the following chemical structure:

Stabilized β-Carotene

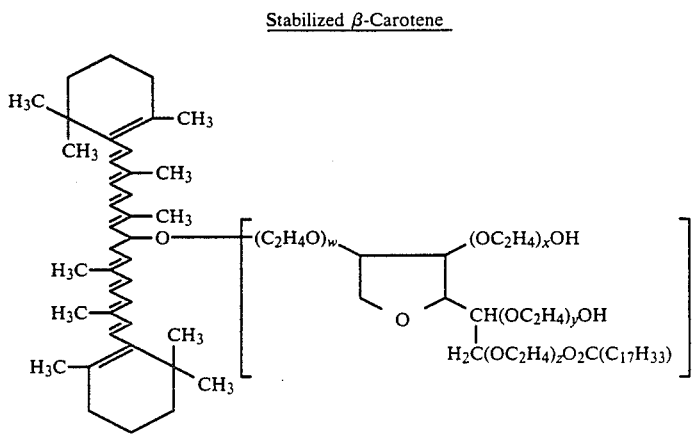

where; w + x + y + z = 20

The following example is given in order to illustrate the invention, but is not to be construed in limitation thereof.

EXAMPLE 1

Polysorbate (91 parts) is heated with an antioxidant (BHT) under normal atmospheric pressure and at a temperature of about 110° C. under an inert argon atmosphere until substantially all of the water has been separated off from the polysorbate.

Once the water has been removed 2.2 parts of B-Carotene are added while the same conditions as aforesaid are maintained. When the B-carotene has been completely dispersed throughout the polysorbate, the temperature is increased to about 170° C. The conditions of an inert atmosphere and atmospheric pressure are maintained. The heating is continued for two hours.

Immediately thereafter, there are added 3 parts t-butylhydroquinone (TBHQ) and 3 parts of p-aminobenzoic acid (PABA) under maintenance of the inert atmosphere. The stirring is continued and the solution allowed to cool to below 30° C.

The chemical analysis of the stabilized B-carotene is carried out as follows:

(1) Accurately weigh 500 mg of stabilized B-carotene in a 1 liter volumetric flask.

(2) Add some deionized water and swirl until completely dissolved. Bring volume up to 1 liter with deionized water, cap and mix thoroughly.

(3) Measure the absorbance of the above prepared solution at 448 nanometers (nm) in a suitable UV-Visible spectrophotometer using deionized water as a blank.

(4) Calculate the absorbance coefficient at 448 nm using the following equation:

$$\text{Coefficient}_{448} = \frac{A_{448} \times 1E^6}{\text{conc } SBC \times L}$$

where $A_{448}$ is the absorbance reading at 448 nm, conc SBC is the level of Stabilized B-carotene in parts per million, L is the path length in centimeters.

(5) The absorbance coefficient should not be less than 1700 absorption units-cm²/gm.

The stabilized B-carotene produced in accordance with the invention is useful as a precursor of Vitamin A, as a food additive, as a colorant, for example, a food colorant, and as a medicament for use both in human and animal medicine.

In contrast to the heretofore available B-carotene whose activity is substantially decreased, even when stored in tightly sealed containers, the product produced in accordance with the invention shows a minimal decrease in activity when stored under the same conditions, after sixty (60) days.

What is claimed is:

1. Stabilized B-carotene having the following formula:

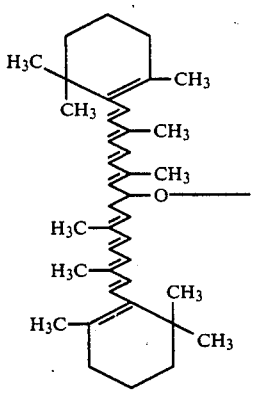

-continued

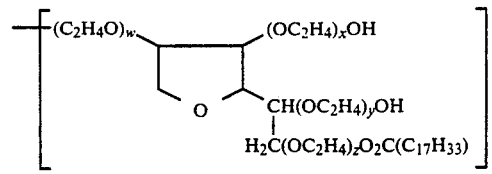

where; $w + x + y + z = 20$

2. Process for the preparation of stable B-carotene which comprises the steps of:
heating 90–99 parts of polysorhate in the presence of an antioxidant under stirring and an inert atmosphere at a temperature in the range of 100°–120° C. until substantially all of the water present in the polysorbate has been removed; introducing 1–10 parts of B-carotene into the polysorbate under stirring, an inert atmosphere and a temperature in the range of 100°–120° C. until all of the B-carotene has been dispersed in the polysorbate;
increasing the temperature to about 160° to about 180° C. while maintaining the inert atmosphere and stirring and continuing the heating at this temperature for about 1 to about 2 hours;
adding 2–5 parts t-butylhydroxyquinone and about 2–5 parts p-aminobenzoic acid to the resultant reaction mixture and under maintenance of the stirring and inert atmosphere allowing the reaction mixture to cool down to below 30° C. and recovering the stable B-carotene thereby formed.

3. Process according to claim 2 which comprises reacting 2.2 parts of B-carotene with 91 parts polysorbate.

4. Process according to claim 2 wherein said polysorbate is a member selected from the group consisting of glyceryl polyoxyethylene glycol ricinoleate, glycerol polyoxyethylene glycol hydroxystearate, polyoxyethylene-20 sorbitan mono-oleate, polyoxyethylene-20 sorbitan mono-laurate, polyoxyethylene-20 sorbitan monostearate and the adduct monohydroxystearic acid with 15 units of ethylene oxide.

5. Process according to claim 2 wherein said antioxidant is a member selected from the group consisting of butylhydroxytoluene, butylhydroxyanisole and d, l-tocopherol.

6. Process according to claim 2 wherein said inert gas is argon or nitrogen.

* * * * *